United States Patent
Schaub et al.

[11] 4,036,980
[45] July 19, 1977

[54] ETHER SUBSTITUTED BENZODIOXAN DERIVATIVES

[75] Inventors: Fritz Schaub, Basel; Hanspeter Schelling, Oberwil, both of Switzerland

[73] Assignee: Sandoz Ltd., Basel, Switzerland

[21] Appl. No.: 581,509

[22] Filed: May 28, 1975

[30] Foreign Application Priority Data
June 5, 1974 Switzerland .......... 7664/74
Apr. 17, 1975 Switzerland .......... 4908/75

[51] Int. Cl.² .......... C07D 319/08; A01N 9/28
[52] U.S. Cl. .......... 424/278; 260/340.3; 260/456 R; 260/609 R; 260/614 R
[58] Field of Search .......... 260/340.3; 424/278

[56] References Cited
U.S. PATENT DOCUMENTS

| | | | |
|---|---|---|---|
| 3,819,655 | 6/1974 | Chodnekar | 260/340.3 |
| 3,829,442 | 8/1974 | Schelling et al. | 260/340.5 |
| 3,910,892 | 10/1975 | Chodnekar et al. | 260/340.3 X |
| 3,910,893 | 10/1975 | Chodnekar et al. | 260/340.3 X |
| 3,912,759 | 10/1975 | Chodnekar et al. | 260/340.3 X |
| 3,933,804 | 1/1976 | Schelling et al. | 260/340.3 X |

FOREIGN PATENT DOCUMENTS

| | | | |
|---|---|---|---|
| 2,523,174 | 12/1975 | Germany | 424/278 |
| 1,357,094 | 6/1974 | United Kingdom | 424/278 |

OTHER PUBLICATIONS
C.A. 77: 164714b.
C.A. 76: 55261k.

*Primary Examiner*—Ethel G. Love
*Attorney, Agent, or Firm*—Gerald D. Sharkin; Richard E. Vila

[57] ABSTRACT

Benzodioxan derivatives of formula,

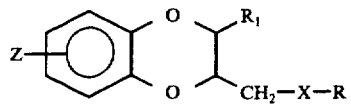

in which
R is a group of formula A

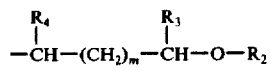

or of formula B,

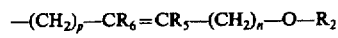

wherein
R$_2$ is a hydrocarbon radical, e.g. alkyl or cycloalkyl,
R$_3$ and R$_4$, independently, are hydrogen or alkyl,
R$_5$ and R$_6$, independently, are hydrogen or methyl,
m, n and p are integers,
R$_1$ is hydrogen or alkyl,
X is oxygen or sulphur
and
Z is hydrogen or a substituent, e.g. alkyl, are useful as insect and acarid growth inhibiting agents.

29 Claims, No Drawings

ETHER SUBSTITUTED BENZODIOXAN DERIVATIVES

The present invention relates to benzodioxan derivatives, more particularly 2-alkoxymethyl- and 2-alkythiomethyl-benzodioxan derivatives, which possess insect and acarid growth inhibiting properties.

Accordingly, there are provided compounds of formula I,

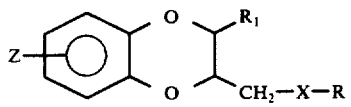

in which R is a group of formula A,

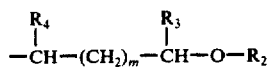

or of formula B,

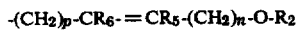

wherein $R_2$ is $C_1-C_{11}$ alkyl, a $C_3-C_{11}$ mono- or multi-unsaturated aliphatic hydrocarbon radical, $C_5-C_7$ cycloalkyl, $C_1-C_6$ alkyl-$C_5-C_7$cycloalkyl, or phenyl, each of $R_3$ and $R_4$, independently, is hydrogen or $C_1-C_4$ alkyl, each of $R_5$ and $R_6$, independently, is hydrogen or methyl, m is an integer of 1 to 6 and each of n and p, independently, is an integer 1 or 2, $R_1$ is hydrogen or $C_1-C_7$ alkyl, X is oxygen or sulphur, and Z is hydrogen, $C_1-C_6$ alkyl, $C_1-C_6$ alkoxy, $C_2-C_7$ alkoxycarbonyl, halogen or nitro, or a group of the formula,

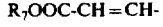

wherein $R_7$ is $C_1-C_6$ alkyl.

In the above definition, it is to be understood that any alkyl radical, either as such or as part of an alkoxy, alkyl-substituted cycloalkyl, or alkoxycarbonyl radical, and any unsaturated aliphatic hydrocarbon radical may be straight or branched chain when containing 3 or more carbon atoms, and may be primary or secondary. Any such radical containing 4 or more carbon atoms may additionally be tertiary.

As will be appreciated the compounds of formula I wherein R is a group B are capable of existing in two geometrical isomeric forms in relation to the -$CR_6=CR_5$-bond. It is to be understood that both such forms as well as mixtures thereof are embraced by the present invention. Such forms may be obtained from mixtures in conventional manner.

Halogen means fluorine, chlorine, bromine or iodine, of which chlorine is preferred.

By the term mono- or multi-unsaturated aliphatic hydrocarbon radical is meant a hydrocarbon radical containing one or more double and/or triple bonds.

When $R_2$ is an unsaturated hydrocarbon radical, this preferably contains 1 or 2 double bonds or 1 triple bond, in particular 1 double bond or 1 triple bond, and preferably is a $C_3-C_6$ especially $C_3-C_5$ hydrocarbon radical.

When $R_2$ in the group of formuoa A or of formula B is alkyl, this is preferably branched chain, more preferably of 3 to 5 carbon atoms, and especially isopentyl, isopropyl, sec.-butyl or tert.-butyl, of which isopropyl and tert.-butyl are the most preferred.

When $R_2$ is cycloalkyl, this is preferably cyclopentyl or cyclohexyl.

When $R_2$ is alkylcycloalkyl, the cycloalkyl moiety, independently, is preferably cyclopentyl or cyclohexyl, and the alkyl moiety, independently, is preferably methyl or ethyl.

Preferably $R_2$, either in the group of formula A or in that of formula B, is alkyl or cycloalkyl, especially alkyl.

In the group of formula A, when each of $R_3$ and $R_4$, independently, is alkyl, this is preferably methyl or ethyl, more preferably methyl.

Preferably each of $R_3$ and $R_4$, independently, is hydrogen, and most preferably $R_3$ and $R_4$ simultaneously are hydrogen. m is preferably 3 or 4, more preferably 3.

In the group of formula B, independently, $R_5$ is preferably methyl, $R_6$ is preferably hydrogen, n is preferably 2 and p is preferably 1.

When $R_1$ is alkyl, this is preferably methyl or ethyl, more preferably methyl. The preferred significance of $R_1$, however, is hydrogen. X is preferably oxygen.

When Z is alkyl, this is preferably $C_1-C_4$ alkyl, especially ethyl, isopropyl or tert.-butyl, when alkoxy, $C_1-C_4$ alkoxy, especially methoxy, ethoxy, isopropoxy or tert.-butoxy, and when alkoxycarbonyl, $C_2-C_5$ alkoxycarbonyl, especially methoxycarbonyl, ethoxycarbonyl, isopropoxycarbonyl or tert.-butoxycarbonyl. In the case where Z is a group of the formula $R_7OOC-CH=CH-$, $R_7$ is preferably $C_1-C_4$ alkyl, especially methyl or ethyl. The preferred significances of Z, however, are hydrogen and alkyl, of which hydrogen is more preferred.

Thus especially preferred compounds of formula I are the following:

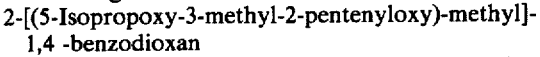

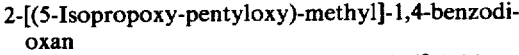

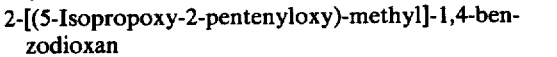

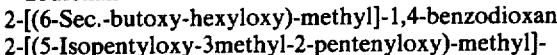

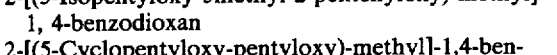

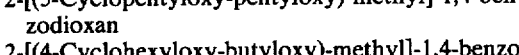

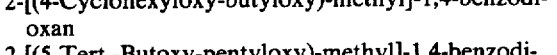

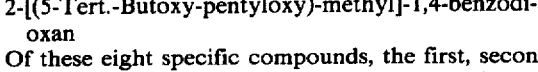

Of these eight specific compounds, the first, second- and eighth-mentioned are particularly preferred.

The present invention alos provides a process for the production of compounds of formula I, which comprises a. condensing together compounds of formulae II and III,

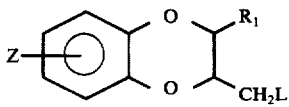 M—R

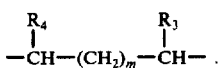

II  III in which R, R₁ and Z are as defined above,
and one of L and M is a group —XH, —XNa or —XK, wherein X is as defined above, and the other is a suitable leaving group under the conditions of the condensation reaction, in the presence of an acid acceptor when one of L and M is the group —XH, or b. condensing together compounds of formulae IV and V,

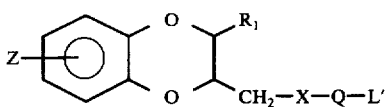 M'—R2

IV  V in which
R₂, R₁, X and Z are as defined above,
Q is a group of the formula,

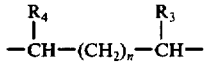

or of the formula,

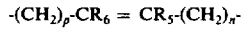

wherein
R₃, R₄, R₅, R₆, m, n and p are ad defined above, and one of

L' and M' is a group —OH, —ONa or —OK, and the other is a suitable leaving group under the conditions of the condensation reaction, in the presence of an acid acceptor when one of L' and M' is the group —OH.

Suitable leaving groups signified by L, M', L' or M' as appropriate, include chloro, bromo, alkylsulphonyloxy and arylsulphonyloxy, particularly preferred examples of the latter two groups being mesyloxy (methylsulphonloxy) and tosyloxy (p-toluenesulphonyloxy). Amongst the numerous leaving groups capable of participating in the variants a) and b) of the above process of the invention, chloro, bromo, mesyloxy and tosyloxy are the preferred leaving groups.

It is to be understood that when, in variant a), L is a group —XH, —XNa or —XK and R is a group of formula B, as defined above, then M cannot in these cases be an alkylsulphonyloxy or arylsulphonyloxy leaving group. Similarly, when, in variant b), M' is a group —OH, —ONa or —OK and Q is a group of the formula —(CH₂)ₚ—CR₆ = CR₅—(CH₂)ₙ—, then L' cannot in these cases be an alkylsulphonyloxy or arylsulphonyloxy leaving group.

In the variant (b), a compound of formula I in which R is a group of formula A is produced when Q in the starting material of formula IV is a group of the formula $$-\overset{R_4}{\underset{|}{CH}}-(CH_2)_m-\overset{R_3}{\underset{|}{CH}}-.$$

A compound of formula I in which R is a group of formula B is produced when Q in the starting material of formula IV is a group of the formula —(CH₂)ₚ—CR₆ = CR₅—(CH₂)ₙ—.

The process of the invention, whether by variant (a) or (b), may be effected as follows:

The condensation is effected in a suitable solvent, such as a hydrocarbon solvent, e.g. benzene or toluene, an ether solvent, e.g. dioxan, 1,2-dimethoxyethane or diethyleneglycoldimethylether, a ketone solvent e.g. acetone, a nitrile solvent, e.g. acetonitrile, an acid amide solvent, e.g. dimethylformamide, or in an appropriate mixture of solvents, e.g. selected from those mentioned above, or without a solvent in an excess of the reagent of any of the formulae II, III, IV and V in which each of L, M, L' and M', respectively, is a group —XH, —XH, —OH and —OH, respectively.

In the cases where one of L and M, in variant (a), or one of L' and M', in variant b) is the group —XH or —OH, respectively, an acid acceptor should also be present in the reaction mixture, examples of suitable acid acceptors being sodium hydroxide, potassium hydroxide, sodium methoxide, sodium ethoxide and potassium tert.-butoxide.

Generally the condensation is effected over a period of from 1 to 24 hours at a temperature between −10° and 150° C where a reagent of formula II or IV is used in which L or L', respectively, is a suitable leaving group, and between 0 and 150° C where a reagent of formula III or V is used in which M or M', respectively, is a suitable leaving group. In the cases where X is oxygen, the reaction is preferably effected in a solvent over a period of from 6 to 18 hours at a temperature above room temperature, e.g. between 50° and 80° C, whereas in the cases where X is sulphur, the reaction is preferably effected in a solvent under or at room temperature. When no reaction solvent is used, the reaction period is generally from 1 to 6 hours and the temperature between 100° and 150° C.

For all cases it is generally advantageous to stir the reaction mixture during the condensation.

It is evident that the condensation reaction described above is effected under conditions appropriate to the Williamson synthesis of ethers. The compounds of formula I may be isolated in conventional manner. They are generally colourless oils which can be purified in conventional manner, e.g. through chromatography or distillation, and which can be characterized conventionally.

The production of the compounds of formulae II to V which are sodium alcoholates or thioalcoholates, is advantageously effected in situ at the begining of the condensation through reaction of the corresponding alcohols or thiols with metallic sodium or with a sodium hydride dispersion. When no reaction solvent is used, the sodium or potassium salts, i.e. compounds of formulae II to V in which L, M, L' or M' is —ONa, —OK, —SNa or —SK, as appropraite, are advantageously produced during the condensation through reaction of the corresponding alcohol or thiol with sodium or potassium hydroxide, preferably under an inert atomosphere, e.g. of nitrogen.

The starting materials of formulae II to V employed in variants (a) and (b) of the process of the invention are either known compounds or may be produced in analogy with processes known per se. For example, compounds of formula III in which M is chloro, bromo, mesyloxy or tosyloxy may be produced by reaction of the corresponding compounds of formula III in which M is hydroxyl (themselves produced in accordance with known processes) with halogenation agents or with mesyl or tosyl halides, as appropriate.

It has been found that the compounds of formula I possess insect and acarid growth inhibiting properties in the sense that they exhibit an inhibiting effect on the development of immature insects and acarids from one development stage to the next, to result either in death, reduced oviposition or inhibition of copulation, thereby leading to a reduced insect or acarid population. The insect and acarid growth inhibiting properties are indicated in each of the following tests.

Test (a) : Effect on the development of *Dysdercus fasciatus* larvae (Egyptian cotton worms)

Filter paper is impregnated with a solution of a compound of formula I, e.g. the compounds of Examples 1, 4, 5, 6, 8 and 12 following, to give a concentration of compound on filter paper of 0.1 mgcm². A polystyrene box (200 × 100 × 85 mm) is lined with the sotreated filter paper, and a folded filter paper, which has also been impregnated to the same concentration, is covered with about 30 Dysdercus larvae of the 4th larval stage and introduced into the box. Compressed cotton seeds, as food, and a drinking vessel are also placed in the box. The percentage of larvae which develop into normal adults after 14 to 15 days is then determined.

Test (b) Effect on the development of *Spodopteralitteralis* larvae (cotton stainer) into adults Filter paper is impregnated with a solution of a compound of formula I, e.g. the compounds of Examples 1,4, 5, 6, 8 and 12 following, to give a concentration of compound on the filter paper of 0.1 mg.cm². The compartments of a plastic box are lined with the sotreated filter paper, and into each compartment is placed a spodoptera caterpiller and a piece of artificial material as food. The percentage of larvae which develop into normal adults after 21 days is then determined.

Test (c) Effect on the development of *Tenebrio molitor* pupa (flour beetles) into adults A compound of formula I, e.g. the compounds of Examples 1 to 10 and 11 following, is used in a 1% w/w solution in acetone. 2μl of the solution, containing 20 micrograms of compound, are applied to the abdominal region of the last three segments of fresh pupa (not older than 18 hours) by means of a 1 -microlitre pipette, 10 pupa being used for each test. The treated pupa are maintained in plastic beakers at 28° C. After 10 to 12 days from treatment the numbers of normally developed adults are counted.

Aside from their insect and acarid growth inhibiting effects, the compounds of formula I exhibit only low mammalian toxicity. They are therefore useful as insecticides and acardicides, particularly in applications where low mammalian toxicity is desirable, e.g. in plant protection.

The compounds may be applied to a locus in conventional manner, e.g. strewing, spraying and dusting in composition form. Suitable formulations comprise a compound of formula I in admixture with a carrier, diluent and/or adjuvant in solid or liquid form, e.g. spraying and dusting powders, granulates, liquid sprays and aerosols.

Solid forms may include conventional inert carrier or diluent materials, e.g. talc, diatomaceous earth, bentonite and pumice, or further additives such as cellulose derivatives and conventional binding and adhesive agents.

Liquid forms may include non-phyotoxic diluents and carriers such as alcohols, petroleum and tar-distillates. Emulsions may be made up with e.g. liquid polyglycolethers produced from addition of alkylene oxides and higher molecular weight alcohols, mercaptans or alkylphenols. Adjuvants such as organic solvents used as solvent aids, e.g. ketones, optionally halogenated aromatic hydrocarbons and mineral oils, andor conventional evaporation-reducing agents may be included.

Aside from the aforementioned carriers, diluents and adjuvants, other active agents may be included with the compounds of formula I in both solid and liquid formulations, as well as such further adjuvants as u.v. stabilizers.

Concentrate forms of liquid formulations generally contain between 2 and 90%, preferably between 5 and 50%, by weight of active compound of formula I. Such concentrate forms are generally diluted before use, and the resulting application forms of the formulations generally contain between 0.01 and 0.1% by weight of active compound of formula I.

The active formulations can be prepared in conventional manner, e.g. as follows:

a. 25 Parts by weight of a compound of formula I are mixed with 25 parts by weight of isooctylphenyldecaglycol ether and 50 parts by weight of xylene, whereby a clear solution is obtained which may be readily emulsified in water. The concentrate may be diluted with water to the desired concentration.

b. 25 Parts by weight of a compound of formula I are mixed with 30 parts by weight of isooctylphenyloctaglycol ether and 45 parts by weight of a petroleum fraction having a boiling range of 210°-280° C ($D_{20}$ =0.92). The concentrate may be diluted with water to the desired concentration.

c. 50 parts by weight of a compound of formula I are mixed with 50 parts by weight of isooctylphenyloctaglycol ether. A clear concentrate is obtained, which may be readily emulsified in water and which may be diluted with water to the desired concentration.

The amount of compound of formula I applied to a locus to be treated will vary depending on the compound employed, the mode of application, ambient conditions, and the species of insects or acarids to be combatted. However, with regard to plant protection, satisfactory results are obtained when the compound of formula I is applied to a plant locus in an amount of between 0.35 and 10 kghectare, the application being repeated as required.

The following Examples 1-12 illustrate the production of the compounds of the invention. Temperatures are in degrees Centigrade and are uncorrected.

EXAMPLE 1

2-[(5-Isopropoxy-3-methyl-2-pentenyloxy)-methyl]-1,4-benzodioxan 0.53 g(0.012 moles) of a 55% sodium hydride dispersion in oil are washed with hexane and the washed sodium hydride is covered with a layer of 10mls of 1,2-dimethoxyethane. To the stirred suspension at 20°-25° is added dropwise over a period of 30 minutes a solution of 1.66g(0.01 moles) of 2-hydroxymethyl-1,4-benzodioxan in 20 mls of 1,2-dimethoxyethane, and the mixture is then stirred at 50° for 2 hours. After the mixture has been cooled to 20°, a solution of 2.21 g (0.01 moles) of 1-bromo-5-isopropoxy-3-methyl-2-pentene (a cis / trans mixture) in 20 mls of 1,2-dimethoxyethane is added dropwise, and the resulting mixture is stirred at 70° for 16 hours.

The reaction mixture is subsequently cooled to room temperature, diluted with 100 mls of water and extracted with ether. The ethereal extract is dried over anhydrous sodium sulphate and evaporated, and the residue is chromatographed on diatomaceous earth with a 5:1 mixture of hexane:ethyl acetate. Produced is a 1:2 cis: trans mixture of 2-[(5-isopropoxy-3-methyl-2-pentenyloxy)-methyl]-1,4-benzodioxan, $n_D^{20} = 1.5085$ Analysis: $C_{18}H_{26}O_4$ Molecular weight: 306.4; Calculated: C,70.6%; H,8.6% O,20.9%; Found : C,70.9%, H,8.9%; O,21.0%.

EXAMPLE 2

2-[(5-Isopropoxy-2-pentenyloxy)-methyl]-1,4-benzodioxan

In an analogous manner to that described in Example 1, with the differences that a cis/trans mixture of 1-chloro-5-isopropoxy-2-pentene is used instead of the cis/trans mixture of 1-bromo-5-isopropoxy-3-methyl-2-pentene, the mixture of sodium hydride, 1,2-dimethoxyethane, 2-hydroxy-1,4-benzodioxan and the aforementioned bromopentane derivative is stirred at 80° for 18 hours, and the chromatography is effected with a 9:1 mixture of hexane-ethyl acetate, a 1:4 cis:trans mixture of 2-[(5-isopropoxy-2-pentenyloxy)-methyl]-1,4-benzodioxan, as a pale yellow oil, $n_D^{20} = 1.5090$, is obtained.

Analysis: $C_{17}H_{24}O_4$ Molecular weight:292.4; Calculated: C,69.8%; H,8.3%; O,21.9% Found: C,70.0%; H,8.5%; 0,22.2%.

EXAMPLE 3

2-[(5-Isopentyloxy-3-methyl-2-pentenyloxy)-methyl]-1,4-benzodioxan

In an analogous manner to that described in Example 2, using 1-bromo-5-isopentyloxy-3-methyl-2-pentene instead of 1-chloro-5-isopropoxy-2-pentene, the above-mentioned product is obtained, $n_D^{20} = 1.5067$.

Analysis: $C_{20}H_{30}O_4$ Molecular weight: 334.5; Calculated: C,71.8%; H,9.0%; O,19.1%; Found: C,71.6% H,9.0%; O,19.3%.

EXAMPLE 4

2-[(5-Isopropoxy-pentyloxy)-methyl]-1,4-benzodioxan 0.53 g (0.012 moles) of a 55% sodium hydride dispersion in oil are washed with hexane and the washed sodium hydride is covered with a layer of 10mls of 1,2-dimethoxyethane. To the stirred suspension at 20° C is added dropwise a solution of 1.66 g (0.01 moles) of 2-hydroxymethyl-1,4-benzodioxan in 20 mls of 1,2-dimethoxyethane, and the mixture is then stirred at 60° for 2 hours. A solution of 23 g (0.011 moles) of 1-bromo-5-isopropoxypentane in 20 mls of 1,2-dimethoxyethane is then added to the mixture dropwise over a period of 20 minutes, and the resulting mixture is stirred at 80° for a further 16 hours.

The reaction mixture is subsequently cooled to 20°-25°, diluted with 100mls of water and extracted with ether. The ethereal extract is dried over anhydrous sodium sulphate and evaporated, and the residue is chromatographed on diatomaceous earth with a 5:1 mixture of hexane:ethyl acetate. Produced in gas chromatographically-pure 2-[(5-isopropoxy-pentyloxy)-methyl]-1,4-benzodioxan as a pale yellow oil, $n_D^{20} = 1.4931$.

Analysis: $C_{17}H_{26}O_4$ Molecular weight: 294.4; Calculated: C,69.4%; H,8.9%; O,21.7%; Found: C,69.3% H,9.2%; O,21.8%.

EXAMPLES 5 and 6

The following products are obtained in an analogous manner to the described in Example 4, the starting material and analytical data being given in each case:

| Example | Product | Starting material | $n_D^{20}$ | Molecular weight | Analysis:calc'd/ found (molecular formula) |
|---|---|---|---|---|---|
| 5 | 2-[(6 sec.-butoxy-hexyloxy)-methyl]-1,4-benzodioxan | 1-bromo-6-sec.-butoxy-hexane | 1.4939 | 322.4 | C,70.8/70.7%; H,9.4/9.8%; O,19.8/19.9%; ($C_{19}H_{30}O_4$) |
| 6 | 2-[(5-isopentyloxy-pentyloxy)-methyl]-1,4-benzodioxan | 1-bromo-5-isopentyloxy-pentane | 1.4944 | 322.4 | C,70.8/70.8%; H,9.4/9.5%; O,19.8/20.2%; ($C_{19}H_{30}O_4$) |

EXAMPLE 7

2-[(8-Ethoxy-octyloxy)-methyl]-1,4-benzodioxan

A mixture of 2.37 g(0.01 moles) of 1-bromo-8-ethoxyoctane, 0.4g(0.01 moles) of sodium hydroxide and 1.66 g (0.01 moles) of 2-hydroxymethyl-1,4-benzodioxan is maintained at 140° with stirring for 1 hour. After the mixture has been cooled to room temperature, it is diluted with 50 mls of water and extracted with ether. The ethereal extract is washed with water, dried over anhydrous sodium sulphate and evaporated, and the residue is chromoatographed on diatomaceous earth with a 5:1 mixture of hexane:ethyl acetate. Produced is 2-[(8-ethoxy-octyloxy)-methyl]-1,4-benzodioxan as a colourless oil, $n_D^{20} = 1.4945$.

Analysis: $C_{19}H_{30}O_4$ Molecular weight: 322.4; Calculated: C,70.8%; H,9.4%; O,19.8%; Found: C,70.6%; H,9.1%; O,20.1%.

EXAMPLES 8 to 11

The following products were obtained in an analogous manner to that described in Example 7, the starting material and analytical data being given in each case:

| Example | Product | Starting material | $n_D^{20}$ | Molecular weight | Analysis:calc'd/ found (molecular formula) |
|---|---|---|---|---|---|
| 8 | 2-[(5-cyclopentyloxy-pentyloxy -1,4 -benzodioxan | 1-bromo-5-cyclo-pentyloxy-pentane | 1.5124 | 320.4 | C,71.2/70.9%; H,8.8/8.7%; O,20.0/20.2%; ($C_{19}H_{28}O_4$) |
| 9 | 2-[(5-heptyloxy-penty-loxy)-methyl]-1,4-benzodioxan | 1-bromo-5-n-hepty-loxy-pentane | 1.4900 | 350.5 | C,72.0/72.1%; H,9.8/9.9%; O,18.3/18.0%; ($C_{22}H_{34}O_4$) |
| 10 | 2-[(4-cyclohexyloxy-butyloxy)-methyl]-1, 4-benzodioxan | 1-bromo-4-cyclo-hexyloxy-butane | 1.5148 | 320.4 | C,71.2/71.3%; H,8.8/8.7%; O,20.0/20.2%; ($C_{19}H_{28}O_4$) |
| 11 | 2-[(5-tert.-butoxy-pentyloxy)-methyl]-1,4-dioxan | 5-tert.-butoxy-pentyl-1-toxylate | 1. | 308.4 | C,70.1/70.2%; H,9.2/9.1%; O,20.8/20.6%; ($C_{18}H_{28}O_4$) |

EXAMPLE 12

2-[(5-Isopropoxy-pentylthio)-methyl]-1,4-benzodioxan

To a solution of 0.68 g (0.01 moles) of sodium ethoxide in 20 mls of ethanol are added 1.62g(0.01 moles) of 5-isopropoxy-1-mercapto-pentane. The solvent is evaporated off under reduced pressure and the residue is taken up in 50 mls of 1,2-dimethoxyethane. While the solution is stirred at 20°-25°, 2.44 g (0.01 moles) of 2-mesyloxymethyl-1,4-benzodioxan are added and the mixture is warmed to 60°.

After 16 hours the reaction mixture is cooled to room temperature and poured into water. The mixture is extracted with ether, and the ethereal extract washed with sodium chloride solution, dried over anhydrous sodium sulphate and evaporated.

The residue is chromatographed on silica gel with a 19:1 mixture of hexane:ethyl acetate. Produced is 2-[(5-isopropoxy-pentylthio)-methyl]-1,4-benzodioxan as a gas chromatographically-pure bright yellow oil, $n_D^{20}$ = 1.5264

Analysis:
$C_{17}H_{26}O_3S$ Molecular weight : 310.5; Calculated: C,65.8%; H,8.4%; S,10.3%; Found : C,65.7%; H,8.7%; S,10.4%.

The following Examples 13 to 17 illustrate the production of the starting materials of formula III, in which M is a leaving group, used in some of the above processes for producing the compounds of formula I. Temperatures are in degrees Centigrade and are uncorrected.

EXAMPLE 13

1-Bromo-5-isopentyloxy-3-methyl-2-pentene

To 40 mls of a 48% solution of hydrobromic acid are added dropwise with stirring at 5° during a period of 15 minutes 18.6 g (0.1 moles) of 5-isopentyloxy-3-methyl-1-penten-3-ol. After 30 minutes at 0°-5° the mixture is extracted with ether and the ethereal extract is washed with 10% sodium carbonate solution and then with saturated sodium chloride solution, dried with anhydrous sodium sulphate and evaporated.

The resulting residue of 1-bromo-5-isopentyloxy-3-methyl-2-pentene is used without further purification.

EXAMPLE 14

1-Bromo-5-cyclopentyloxypentane 1.15g(0.05 moles) of sodium in small pieces are added under a nitrogen atmosphere to 43 g (0.50 moles) of absolute cyclopentanol, and the mixture is stirred at 60° until all the sodium is dissolved after a period of 16 hours. After the solution has been cooled to 20°, 11.5 g (0.05 moles) of 1,5-dibromopentane are added and the mixture is stirred under reflux for 18 hours. The precipitated sodium bromide is then removed by filtration and the filtrate is freed of excess cyclopentanol by distillation. The fraction boiling in the temperature range 115°-118°/1.0 mm is collected, and consists of the desired product.

Analysis: $C_{10}H_{19}BrO$ Molecular weight : 235.2; Calculated: C,51.1%; H,8.1%; Br,34.0%; Found : C,51.3%; H,8.0%; Br,34.4%.

EXAMPLES 15 AND 16

The following starting materials of formula V are produced from appropriate starting materials in an analogous manner to that described in Example 14, the analytical data being given in each case:

| Example | Product | Boiling point | Molecular weight | Analysis : calc'd/ found (molecular formula) |
|---|---|---|---|---|
| 15 | 1-bromo-5-n-hepty-loxy-pentane | 72-74° /0.2mm | 265.2 | C,54.3/55.3%; H,9.5/9.7%; ($C_{12}H_{25}BrO$) |
| 16 | 1-bromo-4-cyclo-hexyloxy-butane | 59-60° /0.2mm | 235.2 | C,51.1/51.2%; H,8.1/7.9%; Br,34.0/34.2%; ($C_{10}H_{19}BrO$) |

EXAMPLE 17

5-tert.-Butoxy-pentyl-1-tosylate

To a solution of 3.14g(0.028 moles) of potassium tert.-butoxide in 42 mls of absolute butanol are added at 70° 10.3g(0.025 moles) of pentane-1,5-ditosylate (boiling point 75°-76.5°) within a period of ½ hours. The mixture is then heated under reflux for 20 hours.

The cooled reaction mixture is extracted with chloroform and the separated chloroform extract is washed in succession with water and saturated sodium chloride solution, dried over anhydrous magnesium sulphate and evaporated under reduced pressure at 40°.

Column chromatography of the residue on 300 g of silica gel with a mixed hexane:ethyl acetate eluant ranging in composition from 96:4 to 85:15 results in production of 5-tert.-butoxy-pentyl tosylate as a colourless oil, $n_D^{20} = 1.5017$. Analysis:

$C_{16}H_{26}O_4S$ Molecular weight : 314.4; Calculated: C,61.1%; H,8.3%; S,10.2%; Found : C,62.7%; H,8.7%; S,9.5%.

To produce starting materials of formula III in which R is a group of formula B, as defined above, alcohols of formula ROH may be used. The latter may be produced in accordance or by analogy with the following Example, which serves as an illustration of the production of such alcohols and which relates specifically to the alcohol used as the starting material in the production of the compound of Example 13. Temperatures are in degrees Centigrade and are uncorrected.

EXAMPLE 18

5-Isopentyloxy-3-methyl-1-penten-3-ol

To a stirred mixture of 12g(0.5 moles) of magnesium shavings and 60 mls of absolute tetrahydrofuran at a temperature within the range 40°-45°, under an atmosphere of nitrogen and contained in a flask equipped with an ice-cooled condenser are added dropwise 5 mls of a solution of 53.5 g (0.5 moles) of vinyl bromide in 100 mls of absolute tetrahydrofuran. Upon the initial addition of the vinyl bromide solution, an exothemic reaction ensues, and the dropwise addition is continued at such a rate that the temperature of the mixture is maintained within the range 45°-50°. The addition lasts between 1 and 1½ hours, whereafter the mixture is stirred for a further hour at 50° and then cooled to 0°.

With vigorous stirring, a solution of 63.2 g (0.4 moles) of 4-isopentyloxy-2-butanone in 100 mls of absolute tetrafuran is added to the reaction mixture dropwise over a period of 45 minutes. Following the addition, the reaction mixture is stirred for a further 16 hours at room temperature, and then cooled to 5°-10° 250 mls of a 20% ammonium chloride solution are then added to the cooled reaction mixture over a period of 15 minutes, and the mixture is stirred for 15 minutes.

The reaction mixture is extracted with ether and the ethereal extract is washed with water, dried over anhydrous sodium sulphate and evaporated. On fractional distillation of the resulting residue, the fraction boiling at 67°-71° at 1.0mm is retained, this fraction consisting of 5-isopentyloxy-3-methyl-1-penten-3-ol, $n_D^{20} = 1,4363$.

Analysis: $C_{11}H_{22}O_2$ Molecular weight : 186.3; Calculated: C,70.9%; H,11.9%; Found : C,70.1%; H,11.6%.

Starting materials of formula RSH, may be produced in accordance or by analogy with the following Example, which serves as an illustration of the production of such thiols and which relates specifically to the thiol used as the starting material in the production of the compound of Example 12. Temperatures are in degrees Centigrade and are uncorrected.

EXAMPLE 19

5-Isopropoxy-1-mercapto-pentane

A solution of 4.18 g (0.02 moles) of 1-bromo-5-isopropoxy-pentane and 1.67 g(0.022 moles) of thiourea in 10 mls of ethanol is heated to boiling point and refluxed over a period of 5 hours. After cooling of the solution to room temperature, 1.2 g (0.03 moles) of sodium hydroxide and 12 mls of water are added, and the mixture is then refluxed for 2 hours.

The cooled reaction mixture is poured into dilute sulphuric acid and the aqueous solution extracted with ether. Thereafter the ethereal extract is washed with water, dried over anhydrous sodium sulphate and evaporated, and the residue is distilled to yield a fraction, with a boiling point of 38°/0.5 mm, consisting of virtually pure 5-isopropoxy-1-mercapto-pentane as a colourless oil.

The following compounds are produced in analogous manner to that described in Examples 1 to 12.

| Ex. No. | R1 | R2 | R3 | R4 | m | X | Z |
|---|---|---|---|---|---|---|---|
| 20 | $C_2H_5-$ | $-CH_2CH=CHCH3$ | H | $n-C_3H_7-$ | 1 | O | isopropyl |
| 21 | $n-C_7H_{15}-$ | $-CH_2CH=CH$<br>$\|$<br>$CH_3CH=CH$ | CH3 | $CH_3-$ | 5 | S | 7-$CH_3O-$ |
| 22 | $n-C_4H_9-$ | $-CH_2C\equiv CH$ | $n-C_4H_9-$ | $C_2H_5-$ | 5 | O | 8-$C_2H_5OOC-$ |
| 23 | $-CH_2C(CH_3)3$ | $-CH_2C\equiv CCH_2$<br>$\|$<br>$CH_2=CH$ | H | H | 1 | S | 7-Cl- |
| 24 | $n-C_7H_{15}-$ | 2-pentyl | $CH_3-$ | iso-$C_4H_9-$ | 4 | O | 5-$NO_2-$ |
| 25 | $CH_3-$ | cycloheptyl | H | $C_2H_5-$ | 1 | S | 6-$C_2H_5OOCCH=CH-$ |
| 26 | $n-C_5H_{11}-$ | 4-ethylcyclohexyl | H | iso-$C_3H_7-$ | 6 | O | 8-$nC_5H_{11}OOC$<br>$\|$<br>$CH=CH-$ |
| 27 | H | 3-$n-C_6H_{11}-$cyclopentyl | $C_2H_5-$ | $-C_2H5$ | 5 | S | 7-$C_6H_{13}O-$ |
| 28 | H | $-CH3$ | $CH_3-$ | $CH_3-$ | 3 | O | 7-$C_2H_5-$ |

| Ex. No. | R1 | R2 | n | P | X | Z |
|---|---|---|---|---|---|---|
| 29 | CH3 | $n-C_{11}H_{23}-$ | 1 | 2 | O | 7-Br- |
| 30 | H | $CH_3-$ | 2 | 2 | S | 7-$NO_2-$ |

-continued

| | | | | | | |
|---|---|---|---|---|---|---|
| 31 | n-C$_6$H$_{13}$— | —CH—C≡CH—CH$_3$ with CH$_3$ branch and H | 1 | 1 | O | 8-nC$_4$H$_9$O— |
| 32 | n-C$_4$H$_9$— | 2-n-hexyl | 1 | 2 | S | 5-CH$_3$COO— |
| 33 | iso-C$_5$H$_{11}$— | —CH3 | 2 | 1 | O | 6-Br— |
| 34 | CH$_3$— | —CH$_2$CH$_2$C≡CCH$_2$ with HC≡C branch | 2 | 2 | S | n-C$_5$H$_{11}$— |
| 35 | iso-C$_3$H$_7$— | 4-CH$_3$—cycloheptyl | 1 | 2 | O | n-C$_4$H$_9$OOC—HC=CH |
| 36 | H | C$_6$H$_5$— | 2 | 1 | S | CH$_3$OOC—CH=CH |
| 37 | CH$_3$— | CH$_3$— | 2 | 1 | O | isopropyl |

What is claimed is:

1. A compound of the formula

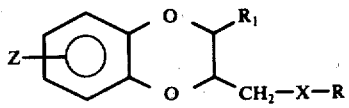

in which R is a group of formula A,

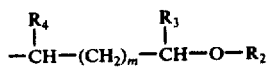

wherein R$_2$ is cyclopentyl or cyclohexyl
each of R$_3$ and R$_4$, independently, is hydrogen or C$_1$-C$_4$alkyl,
each of R$_5$ and R$_6$, independently, is hydrogen or methyl, m is an integer of 1 to 6,
and each of n and p, independently, is an integer 1 or 2,
R$_1$ is hydrogen or C$_1$-C$_7$alkyl,
X is oxygen or sulphur, and
Z is hydrogen, C$_1$-C$_6$alkyl, C$_1$-C$_6$alkoxy, C$_1$-C$_7$ alkoxycarbonyl, halogen or nitro, or a group of the formula,

wherein R$_7$ is C$_1$-C$_6$alkyl.

2. The compound of claim 1 which is 2-[(5-cyclopentyloxy-pentyloxy)-methyl]-1,4-benzodioxan.

3. The compound of claim 1 which is 2-[(4-cyclohexyloxy-butoxy)-methyl]-1,4-benzodioxan.

4. A compound of the formula:

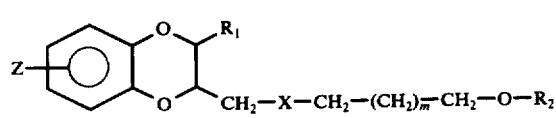

wherein
R$_2$ is C$_1$-C$_{11}$ alkyl, a C$_3$-C$_{11}$ mono- or multi-unsaturated aliphatic hydrocarbon radical, C$_5$-C$_7$ cycloalkyl, C$_1$-C$_6$alkyl-C$_5$-C$_7$cycloalkyl or phenyl,
m is 1 to 6,
R$_1$ is hydrogen or C$_1$-C$_7$ alkyl,
X is oxygen or sulfur, and
Z is hydroden, C$_1$-C$_6$ alkyl, C$_1$-C$_6$ alkoxy, C$_1$-C$_7$ alkoxycarbonyl, halo or nitro, or a group of the formula,

R$_7$OOC—CH=CH— wherein R$_7$ is C$_1$-C$_6$ alkyl.

5. A compound according to claim 4 in which m is 3 or 4.

6. A compound according to claim 4, in which R$_1$ is hydrogen.

7. A compound according to claim 4 in which X is oxygen.

8. A compound according to claim 4, in which Z is hydrogen.

9. The compound of claim 4 which is 2-[(6-sec.butoxy-hexyloxy)-methyl]-1,4-benzodioxan.

10. The compound of claim 4, which is 2-[(5-tert.-butoxy-pentyloxy)-methyl]-1,4-benzodioxan.

11. The compound of claim 4 which is 2-[(5-isopropoxy-pentyloxy)-methyl]-1,4-benzodioxan.

12. An insecticidal or acaricidal formulation comprising an insecticidally or acaricidally effective amount of a compound according to claim 4 in association with an insecticide or acaricide carrier or diluent.

13. A formulation according to claim 12 in liquid concentrate form, which contain 5 to 50% by weight of the compound.

14. A diluted liquid form of a formulation according to claim 12, suitable for application, which contains between 0.01 and 0.1% by weight of the compound.

15. A composition of claim 12 in which the compound is 2-[(5-isopropoxy-pentyloxy)-methyl]-1,4-benzodioxan.

16. A composition of claim 12 in which the compound is 2-[(5-Tert.-butoxy-pentyloxy)-methyl]-1,4-benzodioxan.

17. A method of combating insects or acarids in a locus which comprises applying to the locus an insecticidally- or acaricidally-effective amount of a compound according to claim 4.

18. A method according to claim 17, whereby the compound is applied in an amount of between 0.35 and 10 kg/hectare.

19. The method of claim 17 in which the compound is 2-[(5-isopropoxy-pentyloxy)-methyl]-1,4-benzodioxan.

20. The method of claim 17 in which the compound is 2-[(5-Tert.-butoxy-pentyloxy)-methyl]-1,4-benzodioxan.

21. A compound of the formula:

-continued

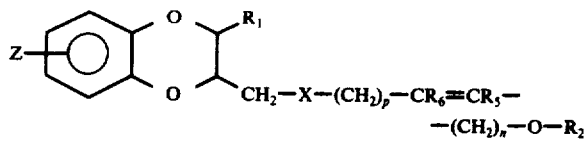

wherein $R_2$ is $C_1$–$C_{11}$ alkyl, a $C_3$–$C_{11}$ mono- or multi- unsaturated aliphatic hydrocarbon radical, $C_5$–$C_7$ cycloalkyl, $C_1$–$C_6$ alkyl-$C_5$–$C_7$ cycloalkyl or phenyl, each of $R_5$ and $R_6$ is independently hydrogen or methyl, each of n and p is independently 1 or 2, $R_1$ is hydrogen or $C_1$–$C_7$ alkyl, X is oxygen or sulfur, and Z is hydrogen, $C_1$–$C_6$ alkyl, $C_1$–$C_6$ alkoxy, $C_1$–$C_7$ alkoxycarbonyl, halo, nitro, or a group of the formula, $R_7OOC$—$CH=CH$— wherein $R_7$ is $C_1$–$C_6$ alkyl.

22. A compound according to claim 21 in which $R_5$ is methyl and $R_6$ is hydrogen.

23. A compound according to claim 21 in which n is 2.

24. A compound according to claim 21, in which p is 1.

25. The compound of claim 21 which is 2-[(5-isopropoxy-3-methyl-2-pentenyloxy)-methyl]-1,4-benzodioxan.

26. The compound of claim 21 which is 2-[(5-isopropoxy-2-pentenyloxy)-methyl]-1,4-benzodioxan.

27. The compound of claim 21 which is 2-[(5-isopentyloxy-3-methyl-2-pentenyloxy)-methyl]-1,4-benzodioxan.

28. A method of combating insects or acarids in a locus which comprises applying to the locus an insectically- or acaricidally-effective amount of a compound of claim 21.

29. The method of claim 28 in which the compound is 2-[(5-isoppropoxy-3-methyl-2-pentenyloxy)-methyl]-1,4-benzodioxan.

* * * * *